(12) United States Patent
Zhang et al.

(10) Patent No.: US 7,914,181 B2
(45) Date of Patent: *Mar. 29, 2011

(54) DISPLAY WITH LIGHTING DEVICE

(75) Inventors: Qiang Zhang, Shenzhen (CN); Xunhua Xiao, Shenzhen (CN); Dongsheng Liang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 12/698,900

(22) Filed: Feb. 2, 2010

(65) Prior Publication Data

US 2010/0220481 A1 Sep. 2, 2010

Related U.S. Application Data

(63) Continuation of application No. 11/871,052, filed on Oct. 11, 2007, now Pat. No. 7,654,704.

(30) Foreign Application Priority Data

Apr. 12, 2007 (CN) ...................... 2007 2 0119538 U

(51) Int. Cl.
*B60Q 3/04* (2006.01)
*F21V 15/00* (2006.01)

(52) U.S. Cl. ............... 362/362; 362/217.11; 362/217.15; 362/249.01; 362/458; 248/918

(58) Field of Classification Search ............. 362/249.02, 362/249.05, 362, 368, 382, 632–634, 800; 349/58; 248/918
See application file for complete search history.

(56) References Cited

U.S. PATENT DOCUMENTS

| 5,815,225 A | * | 9/1998 | Nelson ............................ 349/65 |
| 6,862,472 B2 | | 3/2005 | Mikula et al. |
| 2006/0203481 A1 | | 9/2006 | Kim |

FOREIGN PATENT DOCUMENTS

| CN | 2664041 Y | 12/2004 |
| JP | 60247721 | 7/1985 |

OTHER PUBLICATIONS

Notice of Allowance and Fee(s) Due mailed Aug. 31, 2009, for U.S. Appl. No. 11/871,052, filed Oct. 11, 2007.

* cited by examiner

*Primary Examiner* — Jason Moon Han
(74) *Attorney, Agent, or Firm* — Kory D. Christenser; Stoel Rives LLP

(57) ABSTRACT

The present invention discloses a display with a lighting device comprising a display body having a housing and a power supply panel. The lighting device mounted at the bottom of the housing comprises a transparent base having a receiving cavity and a light source body disposed within the receiving cavity and powered by a power supply. Mounted at the bottom of the display body, the lighting device has the light downwards to illuminate the whole keyboard area of the medical diagnostic device such that the structure is tight without occupying extra space, thereby no inconvenience occurs during doctors' operation. Moreover, the entire lighting device is designed in a modularized manner, and therefore it is convenient for renewal and maintenance.

13 Claims, 4 Drawing Sheets a medical diagnostic apparatus according to the embodiment of the present invention.

DISPLAY WITH LIGHTING DEVICE

STATEMENT OF RELATED APPLICATION

The present application claims the priority of the Chinese Patent Application No. CN200720119538.X, filed on Apr. 12, 2007, entitled "Display with Lighting Device", the disclosure of which is incorporated herein by reference.

FIELD OF THE INVENTION

This invention relates to the field of medical diagnostic apparatuses, and more particularly to a display used in a medical diagnostic apparatus.

BACKGROUND OF THE INVENTION

In order that doctors can read and operate diagnostic apparatuses (such as an ultrasonic diagnostic apparatus) conveniently in a darkroom, a lighting device is required to illuminate the whole keyboard area of the diagnostic apparatus. The lighting devices of the prior art fall into two types: 1) the table lamp available in the market may be directly used as an auxiliary lighting source; 2) a lighting lamp similar to a table lamp may be arranged on one side of the keyboard, the lighting lamp having a supporting bar such that the lighting lamp illuminates the keyboard at a certain height. However, both the two types are deficient in loose structure and extra-occupied space, thereby interfering with normal operations by doctors.

SUMMARY OF THE INVENTION

An objective of the present invention is to provide a display in tight structure without occupying extra space to overcome the deficiencies of the prior art.

According one aspect of the present invention, the technical solution adopted in the present invention for solving the technical problem is to provide a display with a lighting device comprising a display body and a lighting device, wherein the display body has a housing and a power supply panel, and the lighting device mounted at the bottom of the housing consists of a base having a receiving cavity and a light source body disposed within the receiving cavity and powered by a power supply.

The light source body is electrically connected to and powered by the power supply panel of the display body.

The lighting device further comprises a lighting circuit board and a control switch fixed to the base, the lighting circuit board connecting the light source body with the power supply panel via the control switch, the control switch having a first switch link connected to the lighting circuit board and a second switch link connected to the power supply panel.

The base comprises a frame fixed to the bottom of the housing and a light-transparent lamp shade fixed below the frame, above the frame being fixed the lighting circuit board, and the lamp shade and the frame enclosing to form the receiving cavity.

The lighting circuit board has a lamp holder on the side facing the frame, at the position of the frame corresponding to the lamp holder is disposed with a first through hole through which the lamp holder extends into the receiving cavity, and the light source body used as a tube is mounted inside the lamp holder.

The lamp shade has a second through hole, in which the control switch mounted on the frame is exposed.

The frame has a switch fixing hole and the control switch has a resilient fastener, the resilient fastener being fastened into the switch fixing hole.

Part of the wall of the receiving cavity is arc-shaped and reflective.

The housing of the display body comprises a front housing and a rear housing, with a gap formed between the bottoms of the two housings and the lighting device attached within the gap.

According another aspect of the present invention, there is provided a display with a lighting device comprising a display body having a housing and a power supply panel, and a lighting device mounted on the bottom of the housing. The lighting device consists of: a base having a receiving cavity; a light source body disposed within the receiving cavity and powered by a power supply; a lighting circuit board and a control switch mounted on the base, the lighting circuit board connecting the light source body with the power supply panel via the control switch, the control switch having a first switch link connected to the lighting circuit board and a second switch link connected to the power supply panel.

Preferably, the base comprises a frame and a light-transparent lamp shade which enclose to form the receiving cavity, on the frame being mounted the lighting circuit board and the lamp shade being connected to the underside of the frame, the frame having a switch fixing hole into which, the resilient fastener of the control switch is fastened.

Further, the lighting circuit board has a lamp holder, and the light source body is an elongate tube or a LED spot light source mounted within the lamp holder.

Preferably, part of the wall of the receiving cavity is arc-shaped and reflective.

The housing of the display body comprises a front housing and a rear housing, with a gap fainted formed between the bottoms of the two housings, and the lighting device being attached within the gap.

The present invention is conducive to mounting the lighting device at the bottom of the display with the light downwards illuminating the whole keyboard area of the medical diagnostic apparatus such that the structure is tight without occupying extra space, thereby no inconvenience occurs during doctors' operation. Additionally, since the whole lighting device may be mounted within the display in a modularized manner and the control switch employs a resilient fastener for connection, it is convenient for installation, disassembly, renewal and maintenance.

DETAILED DESCRIPTION OF THE INVENTION

Figure 1:
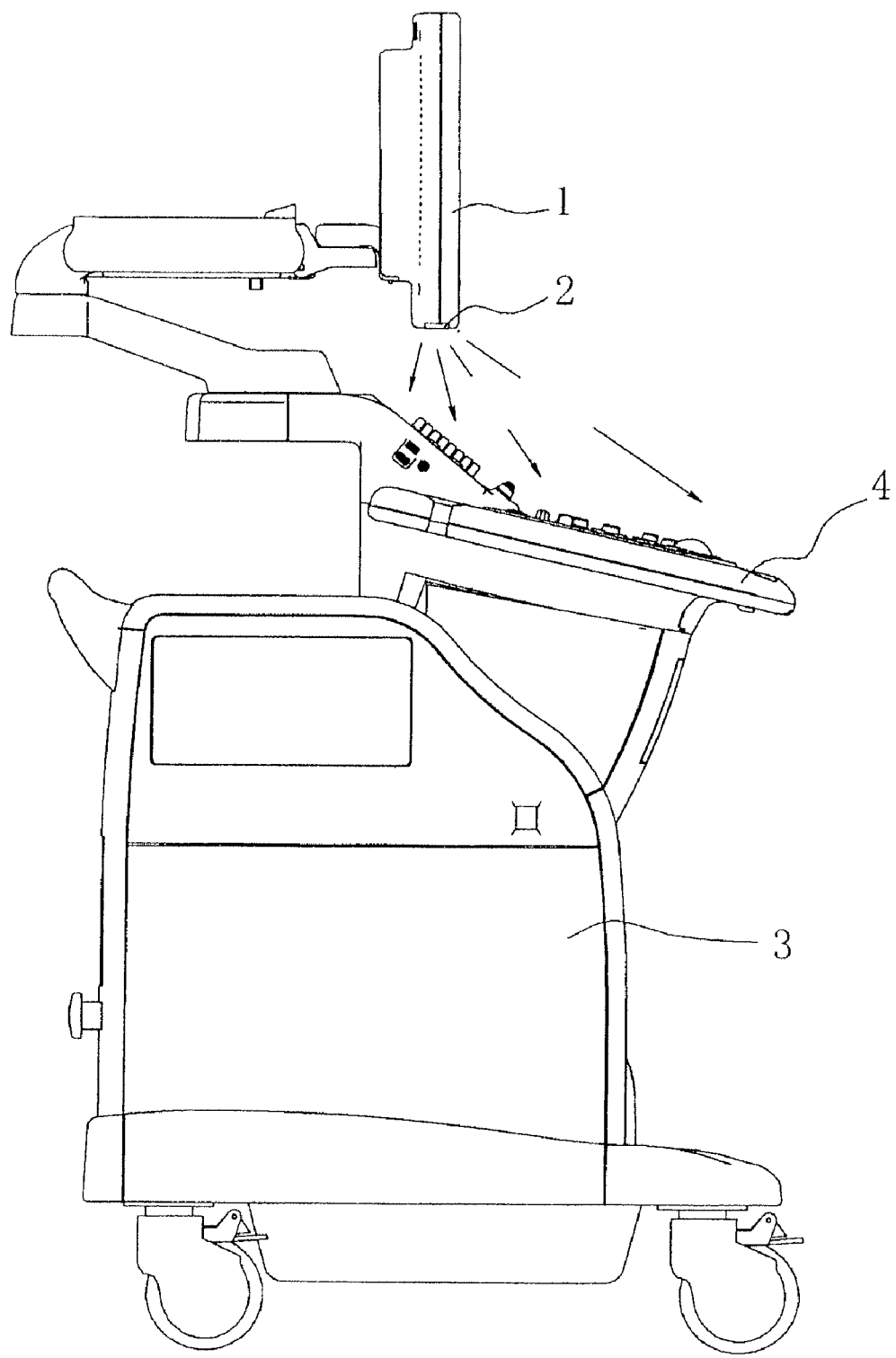
FIG. 1 is a schematic view of the display with a lighting device mounted on a medical diagnostic apparatus according to the embodiment of the present invention.
Figure 2:
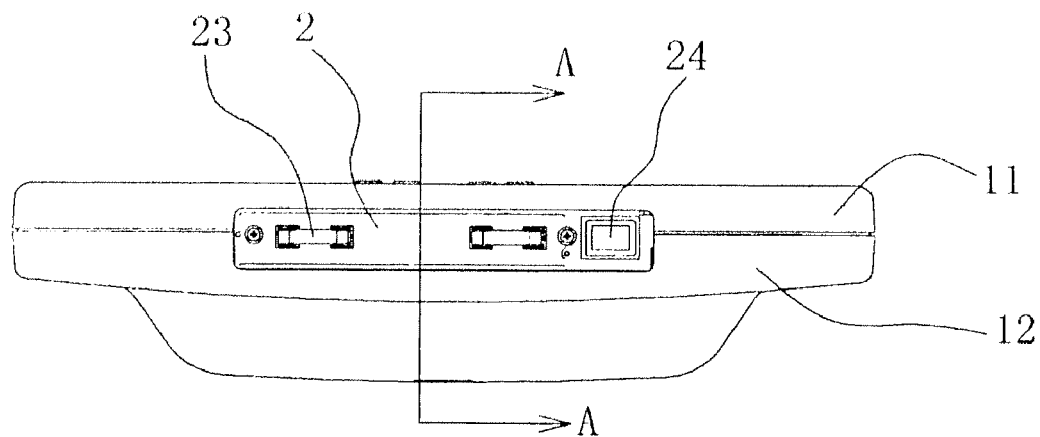
FIG. 2 is a bottom view of the display with a lighting device according to the embodiment of the present invention.
Figure 3:
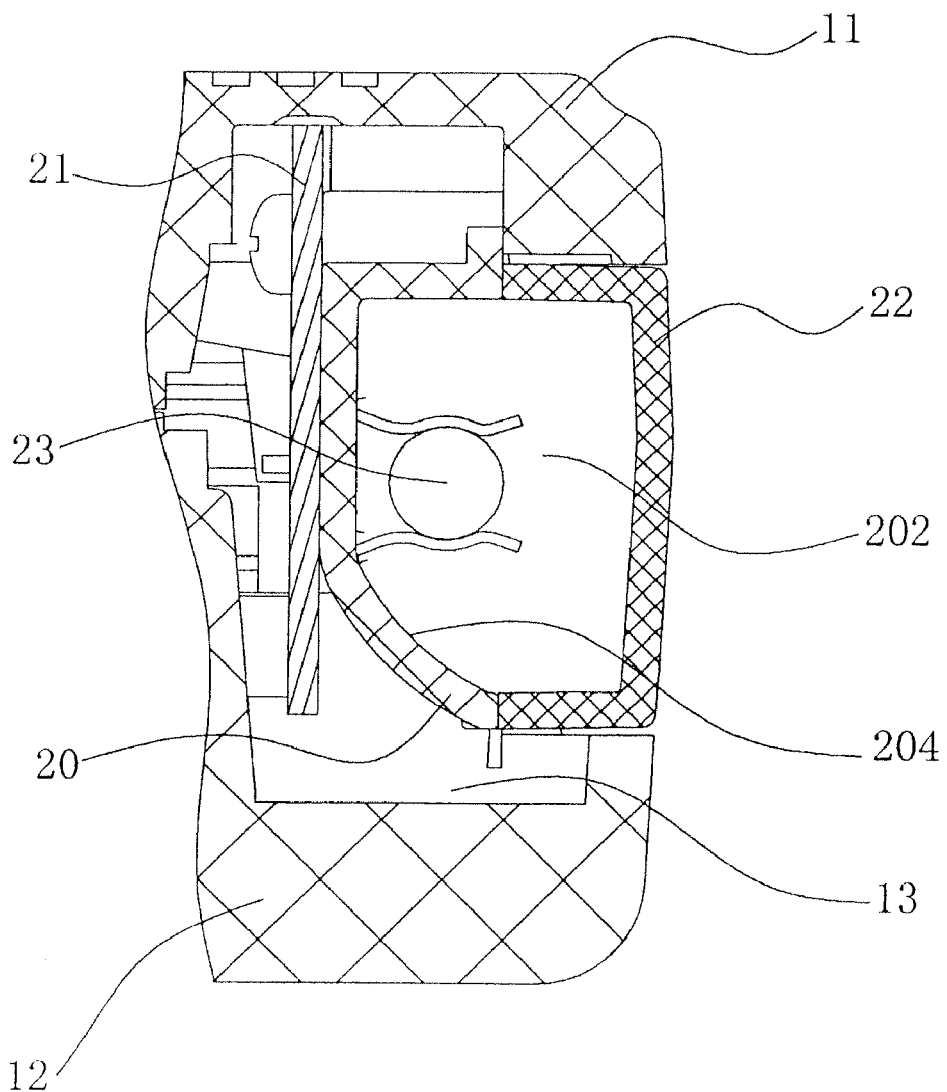
FIG. 3 is a sectional view taken along the line A-A in FIG. 2.
Figure 4:
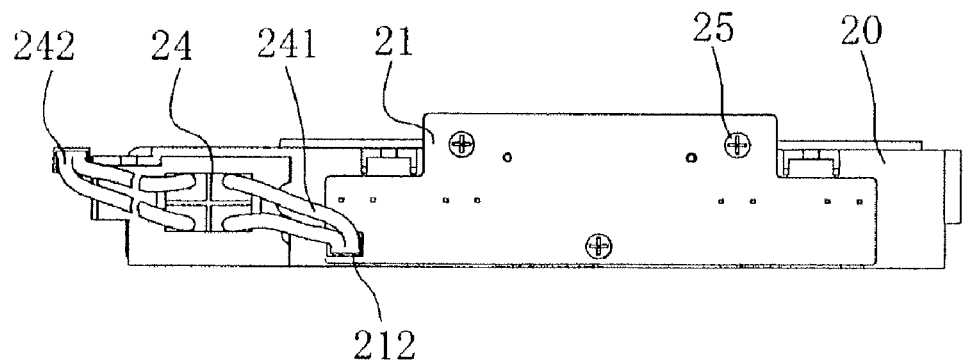
FIG. 4 is a wiring diagram of the control switch of the lighting device according to the embodiment of the present invention.
Figure 5:
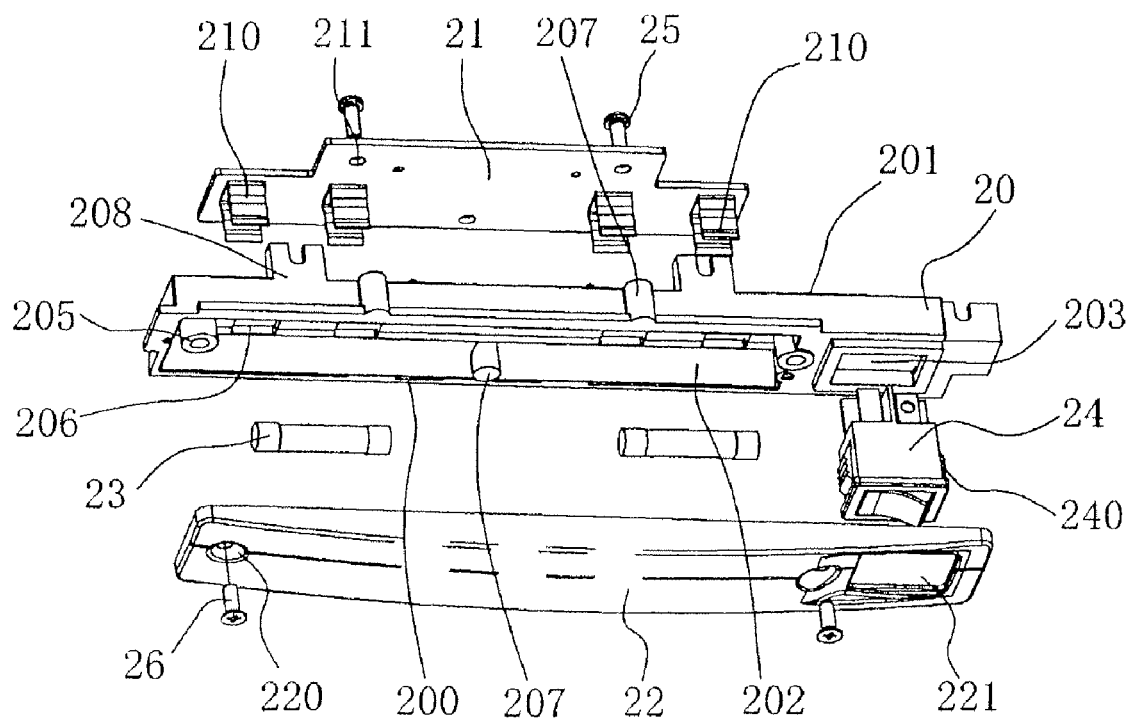
FIG. 5 is an exploded perspective view of the lighting device according to the embodiment of the present invention.
Figure 6:
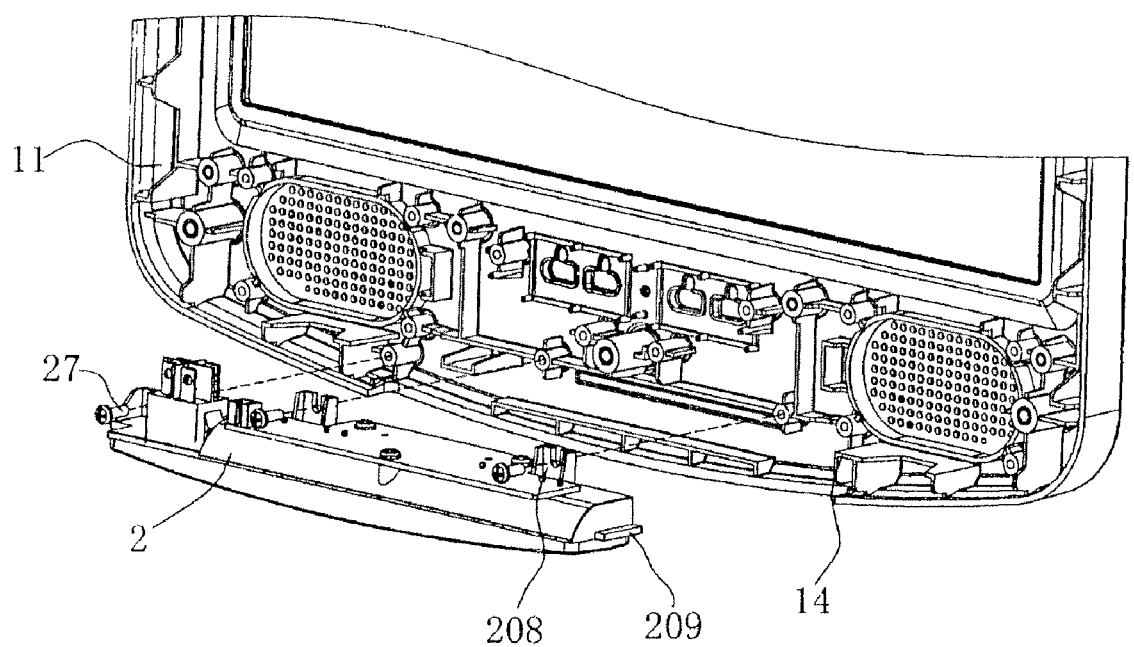
FIG. 6 is schematic view of the lighting device before being mounted in the front housing of the display body according to the embodiment of the present invention.

See FIGS. 1-6. The display with a lighting device according to the embodiment of the present invention comprises a display body 1 and a lighting device 2. The display body 1 comprises a housing and a power supply panel. The housing is constituted by a front housing 11 and a rear housing 12, with a gap 13 formed between the bottoms of the front housing 11 and the rear housing 12. The lighting device 2 is embedded into and fixed in the gap 13. The power supply panel is mounted to the front housing 11.

The lighting device 2 comprises a frame 20, a lighting circuit board 21, a light-transparent lamp shade 22, a pair of tubes 23 and a control switch 24. The frame is made of plastic and has a lower surface 200 facing the lamp shade 22 and an upper surface 201 facing the lighting circuit board 21. The lower surface 200 is provided with a receiving cavity 202 and a switch fixing hole 203 on one side of the receiving cavity 202. Part of the wall 204 of the receiving cavity 202 is arc-shaped and reflective. Two lamp shade fixing poles 205 are disposed at the bottom of the receiving cavity 202. The upper surface 201 is provided with four first through holes 206 arranged in line and communicating with the receiving cavity 202 and three circuit board fixing poles 207 arranged as a triangle The lighting circuit board 21 is provided with four lamp holders 210 respectively aligned with the four first through holes 206 on the side facing the frame 20. The lamp holder 22 is made of transparent plastic, and is provided with countersunk screw bores 220 at the position corresponding to the lamp shade fixing poles 205 of the frame and a second through hole 221 at the position corresponding to the switch fixing hole 203 of the frame. In the middle of the tube 23 lies in a cylindrical glass tungsten filament tube, both ends of which are metal layers snapped tightly to the lamp holder 210 of the lighting circuit board to form a circuit. The control switch 24 is used to control the connection and disconnection of the circuits of the two tubes, having a resilient fastener 240 arranged to snap tightly for installation, a first switch link 241 connected to the lighting circuit board at the end thereof and a second switch link 242 connected to the power supply panel 21 of the display body. In addition, the frame 20 is further provided with three bolt-mounting positions 208 and two hanging ears 209.

The lighting device is installed successively as follows. First, the circuit board 21 is put on the upper surface 201 of the frame, with the four lamp holders 210 thereof respectively passing through the four first through holes 206 of the frame and extending into the receiving cavity 202 of the frame. Then, three screws 25 pass through the through holes 211 of the lighting circuit board and are locked into the three circuit board fixing poles 207 of the frame, thereby fixing the circuit board 21 on the upper surface 201 of the frame. The two tubes 23 are pressed respectively into the four lamp holders 210, with one of them 23 being supported by two lamp holders 210. The control switch 24 is pressed into the switch fixing hole 203 of the frame and snapped tightly via the resilient fastener 240 of the control switch 24. The transparent lamp shade 22 is put on for covering and fixed to the lower surface 200 of the frame using two countersunk bolts 26 passing through the countersunk screw bores 220 of the lamp shade and then being locked into the two lamp shade fixing poles 205 of the frame, thereby the lighting device 2 having the enclosed receiving cavity 202 is assembled.

When mounting the lighting device 2 on the display body 1, the lighting device 2 is fixed to the front housing 11 of the display body using three bolts 27, and the two hanging ears 209 of the frame hang against the rib 14 at the inner side of the bottom of the front housing, thereby the lighting device 2 being fixed reliably to the front housing 11.

The pin of the first switch link 241 of the control switch 24 is plugged into the socket 212 of the lighting circuit board 21, and the first switch link is connected respectively to the two lamp holders of each of the tubes to form a positive electrode and a zero electrode such that lighting voltage is supplied for the tubes via the lighting circuit board. The pin of the second switch link 242 is plugged into the power supply panel of the front housing 11 such that lighting voltage is supplied for the lighting circuit board via the power supply panel.

When in use, the display with a lighting device according to the present embodiment is mounted on the medical diagnostic apparatus 3 (e.g. a bogie type-B ultrasonic). When the tube of the lighting device is lit, part of the light emitted from the tube penetrates directly out of the transparent lamp shade 22, and remaining part penetrates out of the lamp shade 22 after being reflected by the arc-shaped reflective wall 204 of the frame, thereby illuminating the whole keyboard area 4 of the medical diagnostic apparatus.

The present invention is not limited to above embodiments. On the contrary, variations of the present invention are allowed on the basis of the aforementioned. For example, the light source body is not limited to an elongate tube, and other spot light sources such as LED may also be employed. In addition, the transparent lamp shade 22 is not a must, which may be omitted to have the light source body contact directly with the outside. In such a case, since the base is configured to have a receiving cavity 202, the light source body disposed in the concave-receiving cavity 202 may also be protected against damage. Besides, the lighting circuit board 21 may also be disposed on one side of the frame 20 based on requirement, instead of being disposed right above the frame 20 as described hereinbefore.

In the present embodiment, the lighting device is mounted at the bottom of the display body, with the light downwards illuminating the whole keyboard area of the medical diagnostic apparatus such that the structure is tight without occupying extra space, thereby no inconvenience occurs during doctors' operation. As the lighting device is provided with the switch, doctors may readily turn on or off the light if necessary. Also, it is convenient for renewal and maintenance of the tube, as once the service life expires and the tube fails to work, the two countersunk bolts fixing the transparent lamp shade can be loosened and the transparent lamp shade can be removed.

The above contents are details of the present invention with reference to the preferred embodiments and shall not be construed as limitation to the embodiments of the present invention. Those skilled in the art may make simple derivations or replacement under the concept of the present invention, which shall be deemed as being within the scope of the present invention.

What is claimed is:

1. A medical diagnostic apparatus, comprising:
    a display to display medical diagnostic information, the display comprising a display housing having a top edge at an upper end of the display, a bottom edge at a lower end of the display, and a front surface that extends from the top edge to the bottom edge such that the bottom edge extends rearward from the front surface, and wherein the display housing comprises a receiving cavity at a bottom region thereof that is positioned rearward of the front surface of the display housing;
    an input device located below the bottom edge of the display housing; and
    a lighting device disposed within the receiving cavity of the display housing and mounted flush with the bottom edge of the display housing to directly illuminate the input device, wherein the lighting device is oriented relative to the display housing so as to direct light downwardly away from the display and toward the input device.

2. The medical diagnostic apparatus of claim 1, wherein the lighting device comprises at least one tungsten filament tube or light emitting diode (LED).

3. The medical diagnostic apparatus of claim 1, wherein the lighting device is removably attached to the receiving cavity of the display housing.

4. The medical diagnostic apparatus of claim 1, wherein the lighting device includes a transparent lamp shade that is flush with the bottom edge of the display housing.

5. The medical diagnostic apparatus of claim 1, wherein the receiving cavity includes an arc-shaped reflective wall positioned behind the lighting device.

6. The medical diagnostic apparatus of claim 1, wherein the lighting device is electrically connected to a power supply panel within the display.

7. The medical diagnostic claim 6, wherein the lighting device further comprises a lighting circuit board and a control switch, the lighting circuit board connecting the lighting device with the power supply panel via the control switch, the control switch having a first switch link connected to the lighting circuit board and a second switch link connected to the power supply panel.

8. The medical diagnostic apparatus of claim 1, wherein the input device comprises a keyboard.

9. The medical diagnostic apparatus of claim 1, wherein the display housing comprises a front housing and a rear housing, with a gap formed between the bottom edges of the two housings, the lighting device being disposed within the gap.

10. The medical diagnostic apparatus of claim 1, wherein the lighting device comprises at least one tungsten filament tube or light emitting diode (LED) that are positioned such that a portion of light that is emitted therefrom travels to the input device without being reflected.

11. The medical diagnostic apparatus of claim 10, wherein the lighting device comprises a light-transparent lampshade, and wherein said portion of light penetrates directly out of the lampshade.

12. The medical diagnostic apparatus of claim 10, wherein the lighting device comprises a reflective wall, and wherein another portion of light that is emitted from said at least one tungsten filament tube or light emitting diode (LED) is reflected from the reflective wall before traveling to the input device.

13. The medical diagnostic apparatus of claim 10, wherein the lighting device is configured to direct light downwardly away from the display and toward the input device without the light passing through the front surface of the display housing.

* * * * *